United States Patent

Viltro et al.

[11] Patent Number: 5,837,005
[45] Date of Patent: *Nov. 17, 1998

[54] THERMAL PAD HAVING A COMMON ATTACHMENT AND OXYGEN PERMEABLE SIDE

[75] Inventors: L. John Viltro, Hamilton; William R. Ouellette, Cincinnati; Leane K. Davis, Milford, all of Ohio

[73] Assignee: The Procter & Gamble Company, Cincinnati, Ohio

[ * ] Notice: The portion of the term of this patent subsequent to Jun. 27, 2016, has been disclaimed.

[21] Appl. No.: 819,897

[22] Filed: Mar. 18, 1997

Related U.S. Application Data

[63] Continuation of Ser. No. 672,166, Jun. 27, 1996, Pat. No. 5,674,270.

[51] Int. Cl.⁶ ..................................................... A61F 7/00
[52] U.S. Cl. .......................... 607/112; 607/108; 607/96; 607/109; 607/110; 607/112; 165/46
[58] Field of Search ..................................... 607/108, 109, 607/110, 111, 112, 113, 114; 165/46, DIG. 44–DIG. 47, DIG. 49; 126/263.02

[56] References Cited

U.S. PATENT DOCUMENTS

| | | | |
|---|---|---|---|
| Re. 32,026 | 11/1985 | Yamashita et al. | 126/263 |
| 3,149,943 | 9/1964 | Amador | 62/4 |
| 3,667,462 | 6/1972 | Moon | 128/169 |

(List continued on next page.)

FOREIGN PATENT DOCUMENTS

| | | |
|---|---|---|
| 0 014 300 A1 | 8/1980 | European Pat. Off. |
| 0 324 578 A1 | 7/1989 | European Pat. Off. |
| 0 370 600 A1 | 5/1990 | European Pat. Off. |
| 0376490 A1 | 7/1990 | European Pat. Off. |
| 0638300 A1 | 2/1995 | European Pat. Off. |
| 2 687 912 A1 | 9/1993 | France |
| 08 098 856 | 4/1996 | Japan |
| 584005 | 6/1947 | United Kingdom |
| 2153657 | 8/1985 | United Kingdom |
| 2 205 496 | 12/1988 | United Kingdom |
| 2 297 470 | 8/1996 | United Kingdom |
| WO 94/00087 | 1/1994 | WIPO |
| WO 94/12125 | 6/1994 | WIPO |

*Primary Examiner*—Jennifer Bahr
*Assistant Examiner*—Stephen Huang
*Attorney, Agent, or Firm*—Jack L. Oney, Jr.; William Scott Andes

[57] ABSTRACT

A disposable thermal pad includes a substantially planar laminate structure having a first side and a second side and a plurality of heat generating cells embedded between the first and the second sides. The plurality of heat generating cells each are spaced apart and fixedly attached to the laminate structure. The laminate structure provides oxygen permeability to each of the plurality of heat generating cells. Oxygen permeability is achieved entirely on the first side of the laminate structure. The disposable thermal pad is releasably attachable to an inside portion of a user's clothing. The disposable thermal pad is releasably attachable on its first side of the laminate structure so that the second side of the thermal pad may be placed directly against a user's body.

10 Claims, 2 Drawing Sheets

U.S. PATENT DOCUMENTS

| | | | |
|---|---|---|---|
| 3,893,460 | 7/1975 | Karami | 128/287 |
| 3,900,035 | 8/1975 | Welch et al. | 128/402 |
| 3,955,575 | 5/1976 | Okuda | 128/284 |
| 4,044,773 | 8/1977 | Baldwin, III | 128/402 |
| 4,190,054 | 2/1980 | Brennan | 128/402 |
| 4,204,543 | 5/1980 | Henderson | 128/402 |
| 4,366,804 | 1/1983 | Abe | 165/46 |
| 4,413,624 | 11/1983 | Snow | 607/108 |
| 4,516,564 | 5/1985 | Koiso et al. | 126/263 |
| 4,527,566 | 7/1985 | Abare | 128/402 |
| 4,575,097 | 3/1986 | Brannigan et al. | 128/402 |
| 4,586,506 | 5/1986 | Nangle | 128/403 |
| 4,628,932 | 12/1986 | Tampa | 128/402 |
| 4,706,658 | 11/1987 | Cronin | 128/77 |
| 4,756,299 | 7/1988 | Podella | 126/263 |
| 4,802,667 | 2/1989 | Altner | 272/123 |
| 4,805,620 | 2/1989 | Meistrell | 128/402 |
| 4,860,748 | 8/1989 | Chiurco et al. | 128/399 |
| 4,886,063 | 12/1989 | Crews | 128/403 |
| 4,891,501 | 1/1990 | Lipton | 219/527 |
| 4,972,832 | 11/1990 | Trapini et al. | 128/402 |
| 5,000,176 | 3/1991 | Daniel | 128/402 |
| 5,027,801 | 7/1991 | Grim | 128/80 H |
| 5,046,479 | 9/1991 | Usui et al. | 165/46 |
| 5,062,269 | 11/1991 | Siegel | 62/4 |
| 5,080,166 | 1/1992 | Haugeneder | 165/46 |
| 5,086,629 | 2/1992 | Dibrell | 62/259 |
| 5,086,761 | 2/1992 | Ingram | 602/26 |
| 5,088,549 | 2/1992 | Schneider | 165/46 |
| 5,094,238 | 3/1992 | Gibbon | 128/403 |
| 5,133,348 | 7/1992 | Mayn | 128/403 |
| 5,179,944 | 1/1993 | Mcsymytz | 128/403 |
| 5,190,033 | 3/1993 | Johnson | 128/403 |
| 5,366,491 | 11/1994 | Ingram et al. | 607/108 |
| 5,378,225 | 1/1995 | Chatman, Jr. | 602/19 |
| 5,398,667 | 3/1995 | Witt | 126/263 |
| 5,399,130 | 3/1995 | Saunders | 602/19 |
| 5,451,201 | 9/1995 | Prengler | 602/26 |
| 5,496,357 | 3/1996 | Jensen et al. | 607/108 |
| 5,500,959 | 3/1996 | Yewer, Jr. | 602/19 |
| 5,534,021 | 7/1996 | Dvoretzky et al. | 607/112 |
| 5,674,270 | 10/1997 | Viltro et al. | 607/112 |
| 5,728,146 | 3/1998 | Burkett et al. | 165/46 |
| 5,741,318 | 4/1998 | Ouellette et al. | 165/46 |

10
THERMAL PAD HAVING A COMMON ATTACHMENT AND OXYGEN PERMEABLE SIDE

This is a continuation of application Ser. No. 08/672,166, filed on Jun. 27, 1996, now U.S. Pat. No. 5,674,270.

FIELD OF THE INVENTION

The present invention relates to thermal pads intended to be attached to a user's clothing on one side and to be held directly against the user's skin on the other side, and more particularly to such thermal pads requiring oxygen permeability to cause heat generation within the pad. Even more particularly, the present invention relates to heating pads intended for relieving menstrual pain.

BACKGROUND OF THE INVENTION

Heating pads and ice packs are common devices used to relieve pain. However, these pain relieving devices are typically inconvenient to use on a regular and extended basis because: thermal energy may not be immediately available when needed; thermal energy may not be released in a controllable or sustainable manner; and/or proper positioning of thermal energy elements may not be maintainable during body movement.

Prior art heating pads are typically reusable and intended to be placed against clothing instead of directly against the user's body. Such pads may be electrically heated or heated by placing a disposable heat generating packet into a pocket of a reusable wrap. Heat-generating packets typically contain an oxidizing chemistry in a single compartment or sack. The heat source is generally large in size and it is isolated from direct body contact in order to avoid skin burns or discomfort due to poor regulation of temperature. As a result of isolation from direct body contact, the thermal benefit is dependent upon the thickness and heat conducting properties of the user's clothing. Electrical heating pads may have temperature adjustability to compensate for the user's clothing, but electrical heating pads do not provide mobility needed for sustained long term wear.

There are several heat generating packets for reusable wraps on the market that have been designed to use an iron oxidation process to generate portable heat. Generally the rate of chemical reaction, and hence heat generation, is controlled by the amount of oxygen which is allowed to reach the chemistry. This is typically achieved by providing at least one surface of the packet with a specific oxygen permeability while all other surfaces are impermeable. A significant portion of the permeable surface may be oxygen permeable in order to provide uniform oxygen delivery to the entire contents of the packet. For example, Medi-Heat™ Heat Pad, distributed by Innovative Dependable Products, Inc. of Atlanta, Ga., is made with a clothing fastening adhesive on one side and an oxygen permeable membrane on the opposite side. This product can be worn on the outside of clothing or on the inside of clothing. When worn on the outside of clothing, the oxygen permeable membrane faces away from the body and fastening adhesive faces the clothing. However, because the product is not held directly against the body, it is insulated from the body by whatever clothing the user is wearing and the body surface temperature is therefore uncomfortable. When worn on the inside of one's clothing, the fastening adhesive faces outward and the oxygen permeable membrane faces the body. When the product is held directly against one's body, the body obstructs air permeation into the product, thereby uncontrollably altering the heat generated by the oxidation process.

OBJECTS OF THE INVENTION

It is an object of the present invention is to provide a thermal pad which has oxygen permeability on the same side as the means for attaching the thermal pad to a user's clothing so that the opposite side of the thermal pad may be worn directly against the user's skin.

It is another object of the present invention to provide a disposable heating pad, which provides instant heating in a controllable and sustainable manner.

SUMMARY OF THE INVENTION

In one aspect of the present invention, a disposable thermal pad comprises a substantially planar laminate structure having a first side and a second side and a plurality of heat generating cells embedded between the first and the second sides. The plurality of heat generating cells each are spaced apart and fixedly attached to the laminate structure. The laminate structure has means for providing oxygen permeability to each of the plurality of heat generating cells. The means for providing oxygen permeability is located entirely on the first side of the laminate structure. The disposable thermal pad also comprises means for releasably attaching the thermal pad to an inside portion of a user's clothing. The means for releasably attaching is located on the first side of the laminate structure so that the second side of the thermal pad may be placed directly against a user's body.

The plurality of heat generating cells preferably has an oxygen activated, heat generating chemistry containing a mixture of powdered iron, powdered activated charcoal, vermiculite, water and salt.

The means for providing oxygen permeability may comprise an impermeable layer of the laminate structure having a pattern of apertures therethrough providing air communication with the heat generating chemistry. Such a pattern of apertures is located over each of the plurality of heat generating cells. The pattern of apertures is sized to control oxygen permeability and thereby control temperature generated in the heat generating cells.

The means for releasably attaching the thermal pad may comprise pressure sensitive adhesive. The laminate structure has an upper edge and a lower edge, and the pressure sensitive adhesive may be placed in parallel stripes extending continuously from the upper edge to the lower edge between the plurality of heat generating cells. Alternatively, the pressure sensitive adhesive is applied in narrow intermittent strands partially covering the first side such that the means for providing oxygen permeability on the first side maintains an acceptable level of oxygen permeability.

The disposable thermal pad may further comprise an air impermeable envelope surrounding the disposable thermal pad. The thermal pad preferably remains sealed inside the air impermeable envelope until a user is ready to apply the thermal pad to the user's clothing. Opening the air impermeable envelope enables oxygen from ambient air to activate the plurality of heat generating cells to generate controlled and sustained heating.

BRIEF DESCRIPTION OF THE DRAWINGS

While the specification concludes with claims which particularly point out and distinctly cairn the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
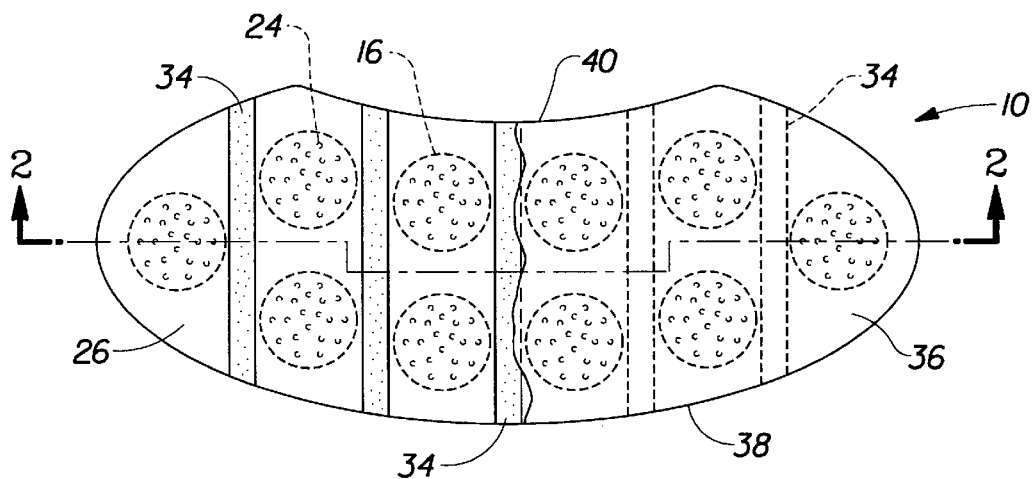
FIG. 1 is a plan view of a thermal pad having a common attachment and oxygen permeable side of the present invention, disclosing a pattern of heat generating cells and attachment adhesive stripes between the cells.
Figure 2:
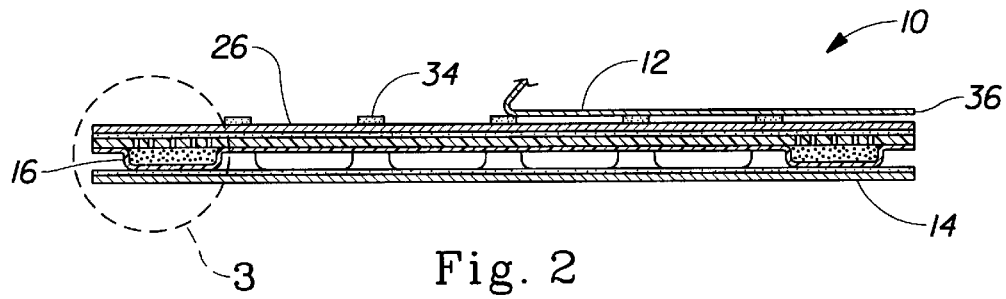
FIG. 2 is cross-sectional view thereof, taken along section line 2—2 of FIG. 1, disclosing the laminated structure of the thermal pad and a release paper protecting the adhesive stripes from premature sticking.
Figure 3:
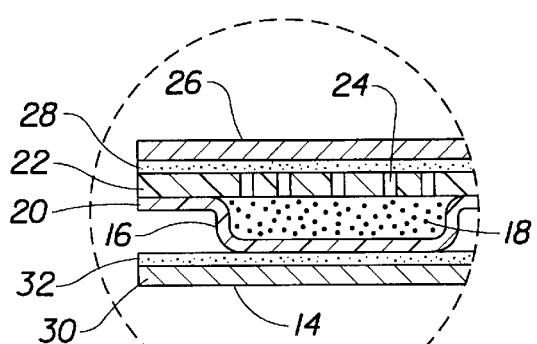
FIG. 3 is an enlarged view of a portion of FIG. 2, taken at dashed circle 3 of FIG. 2, disclosing the laminate structure more clearly.

Referring now to the drawings, and more particularly to FIGS. 1, 2, and 3, there is shown a first preferred embodiment of the present invention, which provides a thermal pad having a substantially planar laminate structure. The laminate structure has a common attachment and oxygen permeable side, and is generally indicated as 10. Thermal pad 10 has a first side 12 which is positioned away from the body during wear and a second side 14 which is positioned against the body. Thermal pad 10 contains a plurality of heat generating cells 16. Heat generating cells 16 contain a chemistry 18, which is embedded in thermal pad 10 by a cell forming layer 20 and a cell covering layer 22. Cell forming layer 20, heat generating chemistry 18, and cell covering layer 22 define heat generating cells 16. Cell forming layer 20 is substantially impermeable to air. Chemistry 18 is activated by oxygen obtained from ambient air. Cell covering layer 22 has an oxygen permeability means 24 for providing oxygen into heat generating cells 16.

The plurality of heat generating cells 16 are spaced apart from each other, and each cell functions independently from the rest. Spacing apart heat generating cells enables the thermal pad to conform to the contours of the body more readily than a single large cell because the chemistry is densely packed in each cell. The chemistry may even be compressed into a tablet in each cell. The cells therefore do not readily flex, but the material between the cells does flex, thereby providing for body conformity.

Preferably, each heat generating cell 16 has a similar volume of chemistry and has a similar oxygen permeability means 24. Alternatively, chemistry volumes, shapes, and oxygen permeability means can be different from cell to cell as long as the resulting cell temperatures generated are similar. The relationship between oxygen permeability and temperature is explained hereinafter.

On either side of heat generating cells 16 are additional layers of material. On first side 12 a first outer fabric 26 is attached to cell covering layer 22 by a first adhesive layer 28. First outer fabric 26 and first adhesive layer 28 are preferably more permeable to air than is cell covering layer 22. Furthermore, first outer fabric 26 and first adhesive layer 28 preferably do not appreciably alter the oxygen permeability of cell covering layer 22. Therefore, cell covering layer 22 alone controls the flow rate of oxygen into each heat generating cell 16.

On second side 14 of thermal pad 10 is a second outer fabric 30, which is attached to cell forming layer 20 by a second adhesive layer 32. Preferably, first outer fabric 26 and second outer fabric 30 are made of similar materials, and first adhesive layer 28 and second adhesive layer 32 are made of the same materials.

First side 12 of thermal pad 10 has an attachment means 34 for releasably attaching thermal pad 10 to clothing. Attachment means 34 may be an adhesive. If an adhesive, then attachment means 34 may have a release paper 36 attached to the adhesive in order to protect adhesive 34 from prematurely sticking to a target other than the intended user's clothing. Attachment means 34 preferably has a stronger bond to first outer fabric 26 than to either release paper 36 or to any target surface.

Alternatively, attachment means 34 may be an adhesive coated film attached to first outer fabric 26. If the adhesive coated film has standoffs to prevent adhesion until the target surface and the film are pressed together to expose the adhesive, then release paper 36 ay be eliminated. Attachment means 34 may also comprise mechanical fasteners connected to first outer fabric 26, which provide sufficient engagement with different varieties of clothing to enable fixed positioning to be achieved. If mechanical fasteners are used, release paper 36 may also be eliminated.

Figure 4:
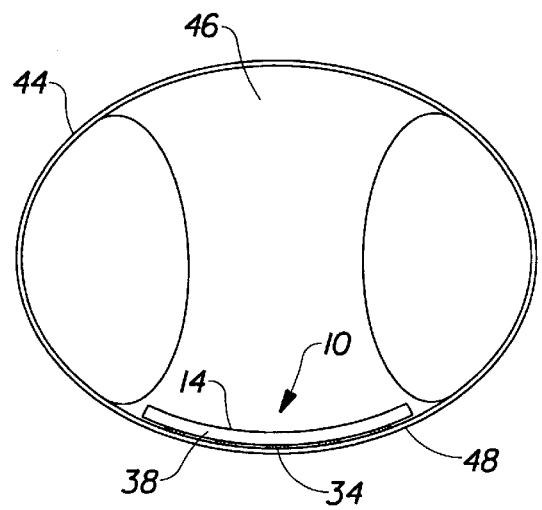
FIG. 4 is a plan view of a pair of women's panties as viewed from the waist end, showing a thermal pad placed on a front panel of the panties so that the thermal pad will deliver heat to the user's abdomen when the panties are worn.

Thermal pad 10 has an upper edge 38 and a lower edge 40 opposite the pad from upper edge 38. These edges are so designated because of the orientation of the pad when it is used as a menstrual pain heating pad and placed inside a woman's panties to rest against her abdomen. FIG. 4 shows a pair of panties 44 having crotch 46 and front panel 48. Adhesive stripes 34 are use to attach thermal pad 10 to front panel 48 after release paper 36 has been removed. Thermal pad 10 is preferably oriented with upper edge 38 located near the waistband of panties 44. In this situation thermal pad 10 serves as a menstrual pain relief heating pad.

Other uses for thermal pad 10 may be envisioned. For example, thermal pad 10 could be placed inside a sweatband and be used as a headache pain relief heating pad when located at the user's forehead.

Cell forming layer 20 is made of any number of suitable materials including, but not limited to: films of polyethylene, polypropylene, polyester, styrene block copolymers, film coated nonwovens, laminates, and coextrusions. Preferably cell forming layer 20 is made of a low density polyethylene film with a basis weight thickness of 0.001 inches (0.025 mm). A particularly suitable material is P 18-1401 white PE microflex embossed film available from Clopay Plastic Products of Cincinnati, Ohio.

Cell covering 100 is made from any number of suitable materials including, but not limited to: films of polyethylene, polypropylene, polyester, styrene block copolymers, film coated nonwovens, laminates, permeable membranes, and coextrusions. A particularly suitable material is P 18-1401 white PE microflex embossed film available from Clopay Plastic Products of Cincinnati, Ohio.

Oxygen permeability means 24 in cell covering layer 22 is preferably a plurality of apertures in cell covering layer 22, which are made by piercing cell covering layer 22 with hot needles. The size of the apertures is preferably about 0.1 mm to about 0.08 mm diameter, and there are preferably 20 to 60 apertures per heat generating cell. Another preferred method of making apertures is to pierce cell covering layer 22 with cold needles. Alternatively, apertures 24 may be produced by a vacuum forming or a high pressure water jet forming process. Yet another method is making cell covering layer 22 from a microporous membrane or a semipermeable membrane. Such membrane may be combined with a highly porous carrier material to facilitate processing. The oxygen permeability required ranges from about 0.01 cc oxygen per minute per 5 square cm to about 15 cc oxygen per minute per 5 square cm at 21° C. and 1 atm.

Attachment means 34, for releasably attaching thermal pad 10 to clothing, may be any number of suitable adhesives and application patterns. A preferred adhesive is Dispomelt™ 34-5598 pressure sensitive hot melt adhesive available from National Starch and Chemical Company of Bridgewater, N.J. This adhesive may be applied to first outer fabric 26 by slot die coating or printing. In either case it is desirable that the adhesive penetrate into first outer fabric 26 so that the adhesive preferentially sticks to first outer fabric 26 upon removal of thermal pad 10 from the user's clothing after use. The pattern of adhesive produced by this method may be straight parallel stripes extending from upper edge 38 to the lower edge 40 of thermal pad 10, and located between heat generating cells 16, as depicted in FIG. 1. The relatively heavy adhesive stripes are oxygen impermeable. By positioning the stripes of adhesive between heat generating cells 16, oxygen permeability means 24 remains unhindered in its ability to pass oxygen to heat generating cells 16. Release paper 36 is preferably a silicone treated paper, such as AK 89147 FT release paper from Akrosil of Menasha, Wis.

Figure 5:
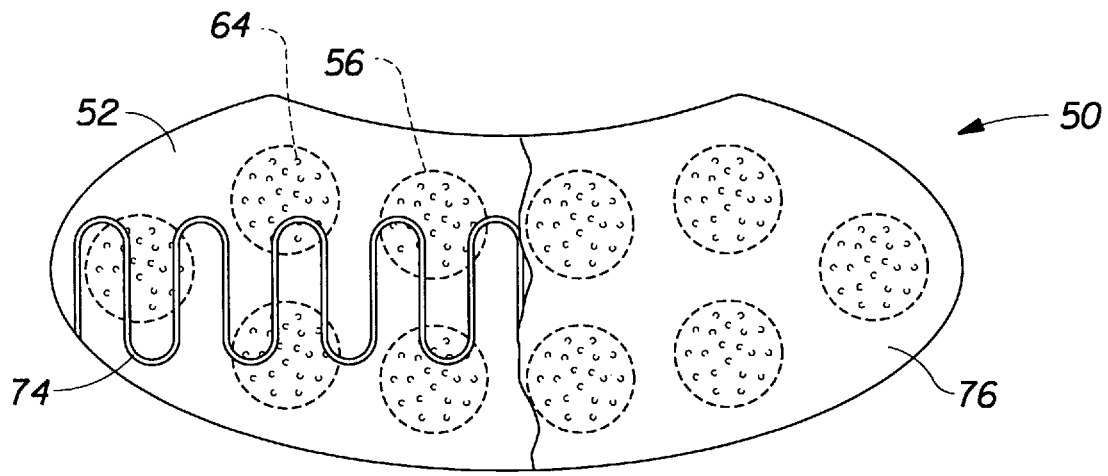
FIG. 5 is a plan view of an alternative thermal pad of the present invention showing a pattern of adhesive other than stripes, which includes partial random coverage of the oxygen permeable surface of the heat generating cells.
Figure 6:
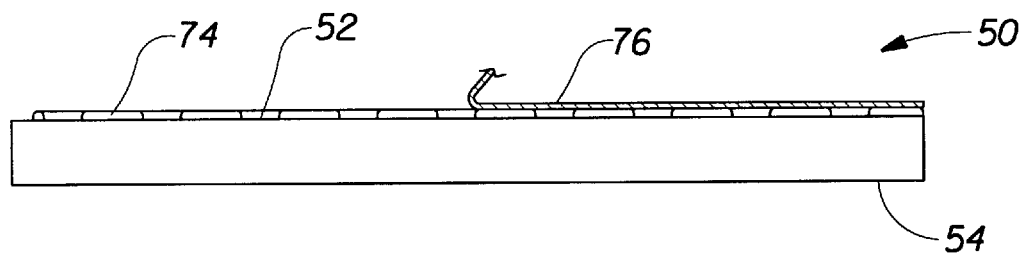
FIG. 6 is a side elevation view thereof, showing the adhesive pattern of FIG. 5 and a release paper protecting the adhesive from premature sticking.

FIGS. 5 and 6 show an alternative embodiment of the thermal pad having a common attachment and oxygen permeable side, and is generally indicated as 50. FIGS. 5 and 6 show an alternative way of delivering an attachment means by spiral, melt blown, or control coat application of pressure sensitive hot melt adhesives in narrow strands. Such a method delivers the adhesive in repeat patterns or in a randomly discontinuous manner.

Thermal pad 50 has a first side 52 which is positioned away from the body during wear and a second side 54 which is positioned against the body. Thermal pad 50 contains a plurality of heat generating cells 56. Heat generating cells 56 contain a chemistry which is embedded in thermal pad 50 by a cell forming layer and a cell covering layer, not shown. Heat generating cells 56 have an oxygen permeability means 64 for providing oxygen into heat generating cells 56. The plurality of heat generating cells 56 are spaced apart from each other, and each cell functions independently from the rest.

A clothing attachment means 74 is shown on first side 52. Clothing attachment means 74 is preferably narrow pressure sensitive adhesive strands or fibrils attached to an outer fabric. First side 52 of thermal pad 50 has a release paper 76 attached to adhesive strands 74 in order to protect adhesive strands 74 from prematurely sticking to a target other than the intended user's clothing. Attachment means 74 preferably has a stronger bond to the outer fabric than to either release paper 76 or to any target surface. This is achieved by melting the adhesive into the fabric such that mechanical entanglement occurs. The deposition of adhesive fibrils or strands to the outer fabric causes minimal obstruction of oxygen flow into heat generating cells 56, such that there is an acceptable level of oxygen permeability maintained.

In a particularly preferred embodiment of the present invention, first outer fabric 26 is preferably a soft flexible material. Materials suitable as first outer fabric 26 include but are not limited to: formed films; fabrics including wovens, knits, and nonwovens, which are carded, spunbonded, air laid, thermally bonded, wet laid, meltblown, and/or through-air bonded. The material composition of first outer fabric 26 may be cotton, polyester, polyethylene, polypropylene, nylon, etc. A particularly suitable material for first outer fabric 26 is 32 gsm (grams per square meter), hydrophobic, polypropylene nonwoven, which is carded, and thermal bonded fabric available from Fibertech, of Landisville, N.J.

Preferably, second outer fabric 30 is a soft, flexible, non-irritating-to-the-skin material. Materials suitable as second outer fabric 30 include but are not limited to: formed films; fabrics including wovens, knits, and nonwovens, which are carded, spunbonded, air laid, thermally bonded, wet laid, meltblown, and/or through-air bonded. The material of second outer fabric 30 may be cotton, polyester, polyethylene, polypropylene, nylon, etc. A particularly suitable material for second outer fabric 30 is 63 gsm hydrophobic polypropylene, which is carded, thermally bonded nonwoven available from Veratec of Walpole, Mass.

Adhesive layers 28 and 32 are applied in such a manner that they do not interfere with oxygen permeability to heat generating cells 16. A suitable material and application method that has been successfully used is: 2031 pressure sensitive hot melt adhesive available from Findley Adhesives of Milwaukee, Wis., which is applied with spiral glue application system available from Nordson, of Waycross, Ga.

Thermal pad 10 generates heat via the use of a mix of chemicals which undergo an oxidation process during use. Chemistry 18 is preferably a mixture of powdered iron, powdered activated charcoal, vermiculite, water, and salt. Mixtures of this type react when exposed to oxygen, providing heat for several hours. Heat generating cells 16 and their manufacture are described in a copending application entitled "HEAT CELLS", first filed in the U.S. on Jun. 29, 1995, having Ser. No. 08/496,639, which was abandoned and replaced with a continuation-in-part application having the same title, filed Feb. 21, 1996, which has Ser. No. 08/604,694 . Both applications are obligated to be assigned to the assignee of the present application. The latter application is hereby incorporated by reference.

Figure 7:
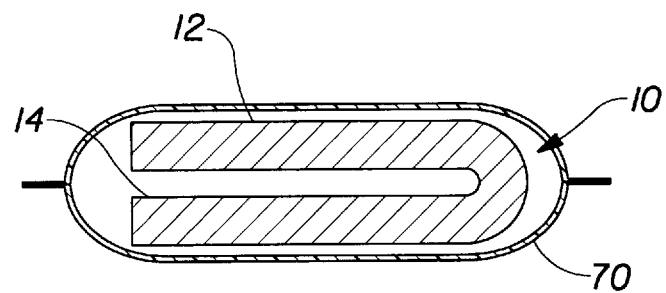
FIG. 7 is a cross-sectional view of the thermal pad of FIG. 1, showing the thermal pad folded inside of an oxygen impermeable package.

Prior to use, thermal pad 10 is enclosed within an oxygen impermeable package 70. Thermal pad 10 is preferably folded in half with second side 14 internal to the fold and external side 12 exposed to the inside of the package, as seen in FIG. 7. Thermal pad 10 is removed from the oxygen impermeable package allowing oxygen to react with chemistry 18. This chemical oxidation system is compact and portable. Once the chemical reaction is completed, the thermal pad is no longer capable of generating heat and it is intended to be appropriately discarded in the solid waste stream. Thus, thermal pad 10 is a disposable item.

Thermal pad 10 solves temperature control problems heretofore experienced by prior art products. Prior art products are intended to be used outside an inner layer of clothing. When there is a layer of clothing between the thermal pad and a user's body, control of temperature delivered to the body surface is impossible because different clothing provides different thermal conductivity.

By placing the attachment means on the same side as the oxygen permeable layer, the thermal pad of the present invention may be worn inside a user's clothing and directly in contact with the user's body. Such direct contact by heat generating cells in the thermal pad provides a known thermal resistance between heat generating chemistry and body surface. Thus, the chemistry can be designed to oxidize at a particular rate to produce a specified temperature. Temperature is particularly important since it has been determined that the body contact temperature must be at least about 39 degrees Centigrade for the average person to experience the sensation of heat. A sustained contact temperature in excess of 45 degrees Centigrade can potentially cause the wearer harm. It is therefore critical to maintain a tight temperature control.

The oxygen permeability that is required to maintain a temperature of 39°–45° C. is very low. Normal clothing is quite porous and offers virtually no resistance to oxygen flow. When the thermal pad of the present invention is worn inside a user's clothing with the oxygen permeable layer and attachment facing outwardly, permeability is unaffected by the presence of even multiple layers of clothing.

The heat generating cells of the present invention are fixedly attached within the thermal pad and are spaced apart from one another. Each cell is provided with a permeable surface which allows oxygen flow into the chemistry such that uniform and complete oxidation of the chemistry occurs independently within each cell. In a preferred embodiment, a heat generating cell size of 25.4 mm diameter by 6.4 mm thick holding 2.8 grams of chemistry yields a temperature of about 41° C. at a body surface for a period of approximately 8 hours when oxygen permeability is 1 cc oxygen per minute per 5 square cm and the thermal pad is exposed to air at 21° C. and 1 atm. This permeability is achieved by punching 26 apertures 0.5 mm diameter in the layer covering each cell.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable thermal pad comprising:
  a) a substantially planar laminate structure having a first side and a second side and a plurality of heat generating cells having an oxygen activated heat generating chemistry embedded between said first and said second sides, said plurality of heat generating cells each being spaced apart and fixedly attached to said laminate structure, said laminate structure having means for providing oxygen permeability to each of said plurality of heat generating cells, said means for providing oxygen permeability located entirely on said first side of said laminate structure; and
  b) means for releasably attaching said thermal pad to an inside portion of a user's clothing, said means for releasably attaching being located on said first side of said laminate structure so that said second side of said thermal pad may be placed directly against a user's body.

2. The disposable thermal pad of claim 1 wherein said means for providing oxygen permeability comprises an impermeable layer of said laminate structure having a pattern of apertures therethrough providing air communication with said heat generating chemistry, said pattern of apertures located over each of said plurality of heat generating cells, said pattern of apertures being sized to control oxygen permeability and thereby control temperature generated in said heat generating cells.

3. The disposable thermal pad of claim 1 wherein said means for releasably attaching said thermal pad comprises pressure sensitive adhesive.

4. The disposable thermal pad of claim 3 wherein said laminate structure has an upper edge and a lower edge, and wherein said pressure sensitive adhesive is placed in parallel stripes extending continuously from said upper edge to said lower edge between said plurality of heat generating cells.

5. The disposable thermal pad of claim 3 wherein said pressure sensitive adhesive is applied in narrow strands partially covering said first side such that said means for providing oxygen permeability on said first side maintains an acceptable level of oxygen permeability.

6. The disposable thermal pad of claim 1 further comprising an air impermeable envelope surrounding said disposable thermal pad, said thermal pad remaining sealed inside said air impermeable envelope until a user is ready to apply said thermal pad to said user's clothing, whereby opening said air impermeable envelope enables oxygen from ambient air to activate said plurality of heat generating cells to generate controlled and sustained heating.

7. A disposable thermal pad comprising:
  a) a substantially planar laminate structure having a first side and a second side and a plurality of heat generating cells embedded between said first and said second sides, said plurality of heat generating cells having an oxygen activated, heat generating chemistry, said laminate structure having having a pattern of apertures providing air communication with said heat generating chemistry, said pattern of apertures located over each of said plurality of heat generating cells, said plurality of heat generating cells each being spaced apart and fixedly attached to said laminate structure said pattern of apertures being sized to control oxygen permeability and thereby control temperature generated in said heat generating cells, said apertures located entirely on said first side of said laminate structure;
  b) pressure sensitive adhesive for releasably attaching said thermal pad to an inside portion of a user's clothing, said pressure sensitive adhesive being located on said first side of said laminate structure so that said second side of said thermal pad may be placed directly against a user's body; and
  c) an air impermeable envelope surrounding said disposable thermal pad, said thermal pad remaining sealed inside said air impermeable envelope until a user is ready to apply said thermal pad to said user's clothing, whereby opening said air impermeable envelope enables oxygen from ambient air to activate said plurality of heat generating cells to generate controlled and sustained heating.

8. The disposable thermal pad of claim 7 wherein said heat generating chemistry contains a mixture of powdered iron, powdered activated charcoal, water and salt.

9. The disposable thermal pad of claim 7 wherein said laminate structure has an upper edge and a lower edge, and wherein said pressure sensitive adhesive is placed in parallel stripes extending continuously from said upper edge to said lower edge between said plurality of heat generating cells.

10. The disposable thermal pad of claim 7, wherein said pressure sensitive adhesive is applied in narrow strands partially covering said first side such that said means for providing oxygen permeability on said first side maintains an acceptable level of oxygen permeability.

* * * * *